(12) United States Patent
Montero et al.

(10) Patent No.: US 9,824,691 B1
(45) Date of Patent: Nov. 21, 2017

(54) AUTOMATED POPULATION OF ELECTRONIC RECORDS

(71) Applicant: Sorenson IP Holdings, LLC, Salt Lake City, UT (US)

(72) Inventors: Adam Montero, Midvale, UT (US); Scot Lorin Brooksby, Highland, UT (US)

(73) Assignee: Sorenson IP Holdings, LLC, Salt Lake City, UT (US)

( * ) Notice: Subject to any disclaimer, the term of this patent is extended or adjusted under 35 U.S.C. 154(b) by 0 days.

(21) Appl. No.: 15/612,644

(22) Filed: Jun. 2, 2017

(51) Int. Cl.
| | |
|---|---|
| *G10L 15/26* | (2006.01) |
| *G10L 15/08* | (2006.01) |
| *G10L 15/18* | (2013.01) |
| *G10L 15/28* | (2013.01) |
| *G10L 15/32* | (2013.01) |
| *G06F 19/00* | (2011.01) |
| *G10L 17/00* | (2013.01) |

(52) U.S. Cl.
CPC .......... *G10L 15/265* (2013.01); *G06F 19/322* (2013.01); *G10L 15/1822* (2013.01); *G10L 15/28* (2013.01); *G10L 15/32* (2013.01); *G10L 17/005* (2013.01); *G10L 2015/088* (2013.01)

(58) Field of Classification Search
CPC ........... G10L 2015/088; G10L 15/1822; G10L 15/26; G10L 15/265; G10L 15/28; G10L 15/32
See application file for complete search history.

(56) References Cited

U.S. PATENT DOCUMENTS

| | | | | |
|---|---|---|---|---|
| 5,960,449 | A * | 9/1999 | Nagaoka | G06F 17/2795 704/10 |
| 6,477,491 | B1 * | 11/2002 | Chandler | G10L 15/26 704/235 |
| 8,458,193 | B1 * | 6/2013 | Procopio | G06F 17/30616 707/749 |

(Continued)

FOREIGN PATENT DOCUMENTS

| | | |
|---|---|---|
| EP | 2288130 A1 | 2/2011 |
| WO | 2010002376 A1 | 1/2010 |

OTHER PUBLICATIONS

"Importance of Transcription in the EHR", http://www.idatamedical.com/importance-of-transcription-in-the-ehr/, Feb. 9, 2017, 5 pages.

(Continued)

*Primary Examiner* — Eric Yen
(74) *Attorney, Agent, or Firm* — Maschoff Brennan

(57) ABSTRACT

A computer-implemented method to populate an electronic record may include generating first transcript data of first audio of a first speaker during a conversation between the first speaker and a second speaker. The method may also include generating second transcript data of second audio of the second speaker during the conversation and identifying one or more words from the first transcript data as being a value for a record field based on the identified words corresponding to the record field and the one or more words being from the first transcript data and not being from the second transcript data. The method may further include providing the identified words to an electronic record database as a value for the record field of a user record of the first speaker.

20 Claims, 7 Drawing Sheets

(56) References Cited

U.S. PATENT DOCUMENTS

| | | | |
|---|---|---|---|
| 8,521,823 B1* | 8/2013 | Sheinberg | 370/227 |
| 9,274,687 B1* | 3/2016 | Meschkat | G06Q 10/109 |
| 9,497,314 B2* | 11/2016 | Milstein | H04M 3/2281 |
| 2002/0091709 A1* | 7/2002 | Jung | G06F 17/30569 |
| 2002/0198719 A1* | 12/2002 | Gergic | G10L 15/22 |
| | | | 704/270.1 |
| 2003/0144885 A1 | 7/2003 | Sachdev | |
| 2003/0146926 A1* | 8/2003 | Valdes | G06F 17/217 |
| | | | 715/703 |
| 2004/0083426 A1* | 4/2004 | Sahu | G06F 17/243 |
| | | | 715/224 |
| 2005/0149364 A1 | 7/2005 | Ombrellaro | |
| 2006/0074652 A1* | 4/2006 | Ativanichayaphong | |
| | | | G06F 17/243 |
| | | | 704/235 |
| 2006/0143157 A1* | 6/2006 | Landsman | G06F 17/2705 |
| 2006/0279760 A1* | 12/2006 | Wang | G06F 21/608 |
| | | | 358/1.14 |
| 2007/0094026 A1* | 4/2007 | Ativanichayaphong | |
| | | | G10L 15/193 |
| | | | 704/257 |
| 2007/0237149 A1* | 10/2007 | Milstein | H04M 3/2281 |
| | | | 370/392 |
| 2008/0177537 A1 | 7/2008 | Ash et al. | |
| 2008/0300856 A1* | 12/2008 | Kirk | B07C 3/00 |
| | | | 704/4 |
| 2009/0048903 A1* | 2/2009 | Lieberman | G06Q 30/02 |
| | | | 705/7.33 |
| 2011/0145013 A1 | 6/2011 | McLaughlin | |
| 2011/0202370 A1 | 8/2011 | Green, III et al. | |
| 2011/0301943 A1 | 12/2011 | Patch | |
| 2012/0173281 A1 | 7/2012 | DiLella et al. | |
| 2012/0258769 A1* | 10/2012 | Nagatomo | H04M 3/42042 |
| | | | 455/550.1 |
| 2012/0323574 A1* | 12/2012 | Wang | G10L 15/22 |
| | | | 704/246 |
| 2013/0138457 A1 | 5/2013 | Ragusa | |
| 2013/0297308 A1* | 11/2013 | Koo | G06F 3/167 |
| | | | 704/235 |
| 2013/0339030 A1 | 12/2013 | Ehsani et al. | |
| 2014/0222462 A1 | 8/2014 | Shakil et al. | |
| 2014/0309987 A1* | 10/2014 | Maddali | G06Q 30/0282 |
| | | | 704/9 |
| 2015/0106091 A1* | 4/2015 | Wetjen | G10L 15/26 |
| | | | 704/235 |
| 2015/0312533 A1 | 10/2015 | Moharir | |
| 2015/0371637 A1 | 12/2015 | Neubacher et al. | |
| 2016/0098521 A1* | 4/2016 | Koziol | G06F 19/322 |
| | | | 704/270.1 |

OTHER PUBLICATIONS

Jeff Klann, "Intelligent Listening 6.872 Final Project", Fall 2006, 16 pages.

"NextPen Solutions allows you to", http://www.nextgen.com/electronic-helaht-records-ehr/productivity-tools/nextpen, retrieved on Apr. 6, 2017, 4 pages.

* cited by examiner

AUTOMATED POPULATION OF ELECTRONIC RECORDS

FIELD

The embodiments discussed herein are related to automated population of electronic records.

BACKGROUND

Communication systems allow participants in different locations to communicate. The communication media used by different communication systems may vary. For example, in some circumstances, communication media in a communication system may be written, audio, video, or some combination thereof. Sometimes, records may be generated based on communications between individuals. For example, information shared between a first individual and a second individual may be memorialized in a record by the first individual, the second individual, or another individual that is part of the communication between the first individual and a second individual.

The subject matter claimed herein is not limited to embodiments that solve any disadvantages or that operate only in environments such as those described above. Rather, this background is only provided to illustrate one example technology area where some embodiments described herein may be practiced.

SUMMARY

A computer-implemented method to populate an electronic record based on communications between two people may include generating, using a processing system, first transcript data of first audio of a first speaker during a conversation between the first speaker and a second speaker. The first transcript data may be a transcription of the first audio. The method may also include generating, using the processing system, second transcript data of second audio of the second speaker during the conversation. The second transcript data may be a transcription of the second audio. The method may further include identifying, using the processing system, one or more words from the first transcript data as being a value for a record field based on the identified words corresponding to the record field and the one or more words being from the first transcript data and not being from the second transcript data. The method may further include providing, over a network, the identified words to an electronic record database as a value for the record field of a user record of the first speaker.

The objects and advantages of the embodiments will be realized and achieved at least by the elements, features, and combinations particularly pointed out in the claims. Both the foregoing general description and the following detailed description are given as examples and are explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Some embodiments of the present disclosure relate to automated population of electronic records based on transcriptions of communication sessions between users. In some embodiments, the present disclosure relates to automated population of electronic health records based on transcriptions of communication sessions between health care professionals and their patients. In these and other embodiments, the communication sessions may occur when the patients and the health care professionals are in the same or different locations.

In some embodiments, a system may be configured to generate a transcription of what is said, e.g., verbally communicated, during a communication session between multiple participants. The system may use the transcription to identify values for fields in electronic records and populate the fields with the values. In some embodiments, the system may generate a transcript for each participant in the communication session based on a networking configuration that obtains the audio generated by the participants during the communication session. As a result, in these and other embodiments, the system may have certainty or a high degree of certainty regarding what was said by each participant in the communication session. This increased certainty regarding what was said by each participant may assist in identifying information from the transcripts of the participants, e.g., a word or phrase, that may populate a field of a record. Furthermore, in some embodiments, the system may be configured to use identifying information from the transcripts for populating general record fields such that specific fields from multiple different record types may be populated using the same information.

In short, the present disclosure provides solutions to problems in artificial intelligence, networking, telecommunications, and other technologies to enhance automated population of records. Embodiments of the present disclosure are explained in further detail below with reference to the accompanying drawings.

Figure 1:
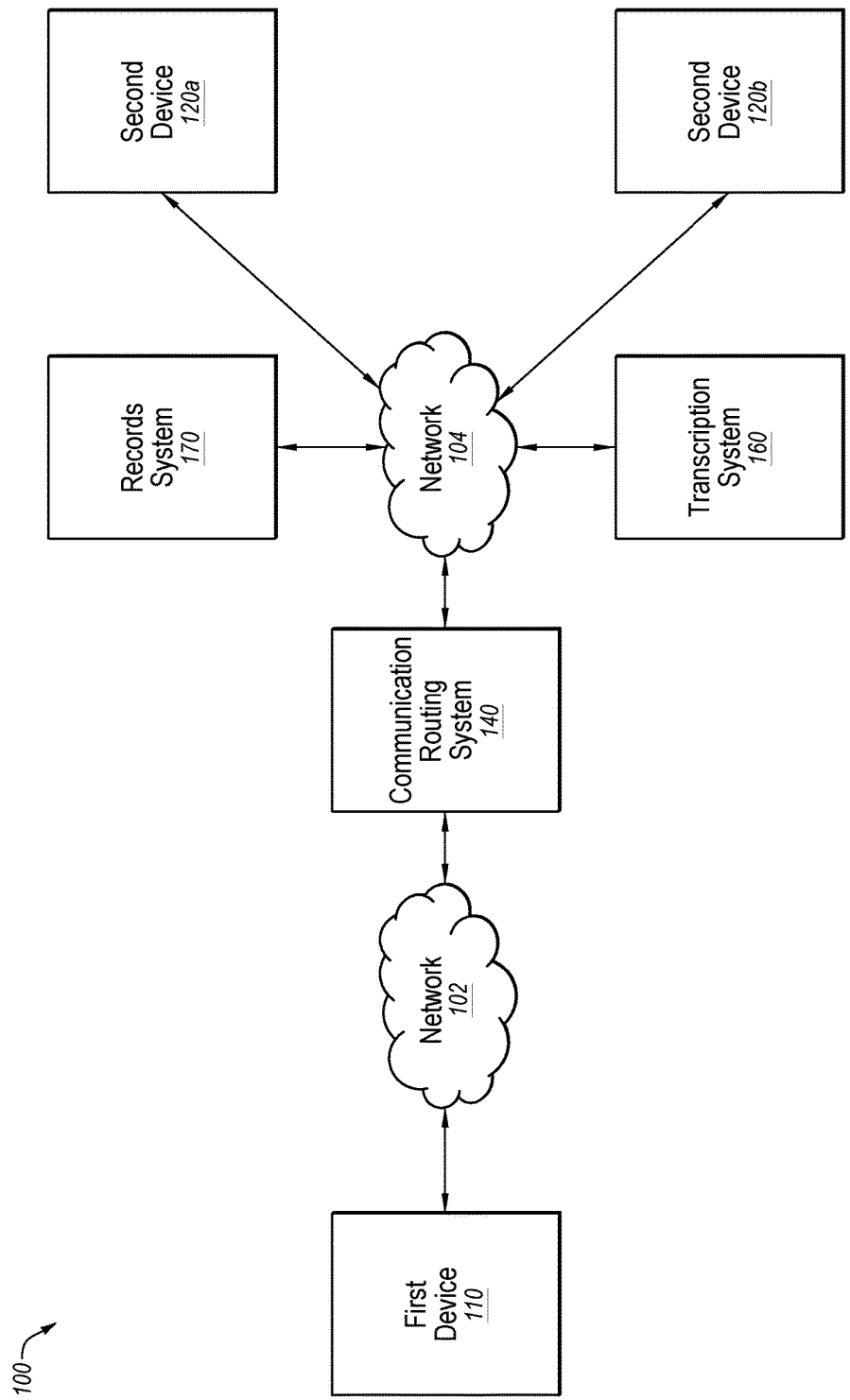
FIG. 1 illustrates an example environment related to transcription and population of electronic records based on device to device communication.

Turning to the figures, FIG. 1 illustrates an example environment 100 related to transcription and population of electronic records based on device to device communication. The environment 100 may be arranged in accordance with at least one embodiment described in the present disclosure. The environment 100 may include a first network 102; a second network 104; a first device 110; second devices 120, including a first second-device 120*a* and a second second-device 120*b*; a communication routing system 140; a transcription system 160; and a records system 170.

The first network 102 may be configured to communicatively couple the first device 110 and the communication routing system 140. The second network 104 may be configured to communicatively couple the second devices 120, the communication routing system 140, the transcription system 160, and the records system 170.

In some embodiments, the first and second networks 102 and 104 may each include any network or configuration of networks configured to send and receive communications between devices. In some embodiments, the first and second networks 102 and 104 may each include a conventional type network, a wired or wireless network, and may have numerous different configurations. Furthermore, the first and second networks 102 and 104 may each include a local area network (LAN), a wide area network (WAN) (e.g., the Internet), or other interconnected data paths across which multiple devices and/or entities may communicate.

In some embodiments, the first and second networks 102 and 104 may each include a peer-to-peer network. The first and second networks 102 and 104 may also each be coupled to or may include portions of a telecommunications network for sending data in a variety of different communication protocols. In some embodiments, the first and second networks 102 and 104 may each include Bluetooth® communication networks or cellular communication networks for sending and receiving communications and/or data. The first and second networks 102 and 104 may also each include a mobile data network that may include third-generation (3G), fourth-generation (4G), long-term evolution (LTE), long-term evolution advanced (LTE-A), Voice-over-LTE ("VoLTE") or any other mobile data network or combination of mobile data networks. Further, the first and second networks 102 and 104 may each include one or more IEEE 802.11 wireless networks. In some embodiments, the first and second networks 102 and 104 may be configured in a similar manner or a different manner. In some embodiments, the first and second networks 102 and 104 may share various portions of one or more networks. For example, each of the first and second networks 102 and 104 may include the Internet or some other network.

The first device 110 may be any electronic or digital device. For example, the first device 110 may include or may be included in a desktop computer, a laptop computer, a smartphone, a mobile phone, a tablet computer, a television set-top box, a smart television, or any other electronic device with a processor. In some embodiments, the first device 110 may include computer-readable-instructions stored on one or more computer-readable media that are configured to be executed by one or more processors in the first device 110 to perform operations described in this disclosure. The first device 110 may be configured to communicate with, receive data from, and direct data to, the communication routing system 140 and/or the second devices 120. During a communication session, audio, video, and/or a transcription of the audio may be presented by the first device 110.

In some embodiments, the first device 110 may be associated with a first user. The first device 110 may be associated with the first user based on the first device 110 being configured to be used by the first user. In these and other embodiments, the first user may be registered with the communication routing system 140 and the first device 110 may be listed in the registration of the first user. Alternatively or additionally, the first device 110 may be associated with the first user by the first user being the owner of the first device 110 and/or being controlled by the first user.

The second devices 120 may be any electronic or digital devices. For example, the second devices 120 may include, or may be included in, a desktop computer, a laptop computer, a smartphone, a mobile phone, a tablet computer, a television set-top box, a smart television, or any other electronic device with a processor. In some embodiments, the second devices 120 may each include, or be included in, the same, different, or combinations of electronic or digital devices. In some embodiments, the second devices 120 may each include computer-readable instructions stored on one or more computer-readable media that are configured to be executed by one or more processors in the second devices 120 to perform operations described in this disclosure.

The second devices 120 may each be configured to communicate, receive data from and direct data to, the communication routing system 140. Alternatively or additionally, each of the second devices 120 may be configured to, individually or in a group, participate in a communication session with the first device 110 through the communication routing system 140. In some embodiments, the second devices 120 may each be associated with a second user or be configured to be used by a second user. During a communication session, audio, video, and/or a transcription of the audio may be presented by the second devices 120 for the second users.

In some embodiments, the second users may be health care professionals. In these and other embodiments, health care professionals may be individuals with training or skills to render advice with respect to mental or physical health, including, nurses, nurse practitioners, medical assistants, doctors, physician assistants, counselors, psychiatrists, psychologists, or doulas, among other health care professionals. In these and other embodiments, the first user may be an individual in their home who has a health care need. For example, the first user may be an individual at home who is recovering from a surgery and who has a need for in-home care from a health care professional. Alternatively or additionally, the first user may be an individual at home who has an illness for which in-home care from a health care professional is preferable. Alternatively or additionally, the first user may be an individual at a care facility or some other facility.

In some embodiments, each of the communication routing system 140, the transcription system 160, and the records system 170 may include any configuration of hardware, such as processors, servers, and databases that are networked together and configured to perform one or more tasks. For example, each of the communication routing system 140, the transcription system 160, and the records system 170 may include multiple computing systems, such as multiple servers that each include memory and at least one processor, which are networked together and configured to perform operations as described in this disclosure, among other operations. In some embodiments, each of the communication routing system 140, the transcription system 160, and the records system 170 may include computer-readable instructions on one or more computer-readable media that are configured to be executed by one or more processors in each of the communication routing system 140, the transcription system 160, and the records system 170 to perform operations described in this disclosure.

Generally, the communication routing system 140 may be configured to establish and manage communication sessions between the first device 110 and one or more of the second devices 120. The transcription system 160 may be configured to generate and provide transcriptions of audio from communication sessions established by the communication routing system 140. The transcription system 160 may also be configured to identify values to populate fields in records in the records system 170 using the transcriptions of audio from the communication sessions.

The records system 170 may be a combination of hardware, including processors, memory, and other hardware configured to store and manage data. In some embodiments, the records system 170 may be configured to store electronic records with various fields. For example, the records system 170 may be configured to store electronic health records (EHR).

An example of the interaction of the elements illustrated in the environment 100 is now provided. As described below, the elements illustrated in the environment 100 may interact to establish a communication session between the first device 110 and one or more of the second devices 120, to transcribe the communication session, and populate fields of an electronic record in the records system 170 based on the transcription of the communication session.

The first device 110 may send a request for a communication session to the communication routing system 140. The communication routing system 140 may obtain the request from the first device 110. In some embodiments, the request may include an identifier of the first device 110.

Using the identifier of the first device 110, the communication routing system 140 may obtain profile data regarding the first user associated with the first device 110. The profile data may include information about the first user, such as demographic information, including name, age, sex, address, etc., among other demographic data. The profile data may further include health related information about the first user. For example, the health related information may include the height, weight, medical allergies, and current medical conditions, etc., among other health related information. The profile data may further include other information about the first user, such as information that identifies the first user with the records system 170, such as a first user identifier. In some embodiments, the profile data may include transcriptions of conversations between the first user and the second users.

Using the profile data and/or other information about the first user, such as medical data about the first user, the communication routing system 140 may select one or more of the second devices 120 for the communication session with the first device 110. After selecting one or more of the second devices 120, the communication routing system 140 may establish the communication session. Alternatively or additionally, the communication routing system 140 may select one or more of the second devices 120 for the communication session with the first device 110 based on one or more of the second devices 120 being identified in the request from the first device 110.

During a communication session, the communication routing system 140 may be configured to receive media data from the first device 110 and the selected one or more of the second devices 120. The communication routing system 140 may route the media data to the transcription system 160 for generation of transcript data. The transcription system 160 may generate transcript data. The transcription system 160 may also analyze the transcript data to determine values for populating fields of a record associated with the first user of the first device 110. The transcription system 160 may send the values to the records system 170 to populate the fields of the records of the first user. The transcript data may also be transmitted to the first device 110 and the selected one or more of the second devices 120 for presentation by the first device 110 and the selected one or more of the second devices 120.

Further explanation of the transcription process and routing is now described. However, it is described in the context of a communication session between the first device 110 and the first second-device 120*a* for ease of explanation.

As mentioned, the first device 110 and the first second-device 120*a* may exchange media data during a communication session. In some embodiments, the media data may include video and audio data. For example, the first device 110 may send first audio data and first video data to the first second-device 120*a* and the first second-device 120*a* may send second audio data and second video data to the first device 110. Alternatively or additionally, the media data may include audio data but not video data.

During the communication session, the media data exchanged between the first device 110 and the first second-device 120*a* may be routed through the communication routing system 140. During the routing of the media data between the first device 110 and the first second-device 120*a*, the communication routing system 140 may be configured to duplicate the audio data from the media data and provide the duplicated audio data to the transcription system 160.

The transcription system 160 may receive the duplicated first audio. The transcription system 160 may generate the first transcript data of the duplicated first audio. The first transcript data may include a transcription of the duplicated first audio.

In some embodiments, the transcription system 160 may generate the first transcript data segments using a machine transcription of the duplicated first audio. In some embodiments, before a machine transcription is made of the duplicated first audio, the duplicated first audio may be listened to and re-voiced by another person. In these and other embodiments, the other person may make corrections to the machine transcription.

The transcription system 160 may provide the first transcript data to the communication routing system 140. The communication routing system 140 may route the first transcript data to the first second-device 120*a*. The first second-device 120*a* may present the first transcript data to a user of the first second-device 120*a* on a display of the first second-device 120*a*.

The communication routing system 140 and the transcription system 160 may handle the second media data from the first second-device 120*a* in an analogous manner. For example, the communication routing system 140 may generate duplicated second audio of second audio of the second media data and the transcription system 160 may generate second transcript data based on the duplicated second audio. The second transcript data may be provided to the first device 110 for presentation of the first user of the first device 110.

In some embodiments, the generation and delivery of the transcript data of the first and second media may both be in substantially real-time or real-time. In these and other embodiments, the first device 110 may present the second transcript data concurrently with the second media data in substantially real-time or real-time. Concurrent presentation of the second transcript data and the second media data in substantially real-time may indicate that when audio is presented, a transcription that corresponds to the presented audio is also presented with a delay of less than 1, 2, 5, 10, or 15 seconds between the transcription and the audio. Alternatively or additionally, the generation and delivery of transcript data of one of the first and second media may be in substantially real-time or real-time and the generation and/or delivery of transcript data of another of the first and second media may not be in real time.

In some embodiments, when a third device, such as the second second-device 120*b* participates in a communication session between the first device 110 and the first second-device 120*a*, third transcript data may be generated for third audio generated by the third device. In these and other embodiments, the third transcript data may be provided to the first device 110 and/or the first second-device 120*a* and the third device may receive the first and/or second transcript data from the first device 110 and the first second-device 120*a*, respectively.

Further explanation of the record field populating process is now described.

After generating the first transcript data of the first audio data and the second transcript data of the second audio data, the transcription system 160 may be configured to use data from the first transcript data and the second transcript data to populate one or more fields of one or more records stored by the records system 170.

Figure 3:
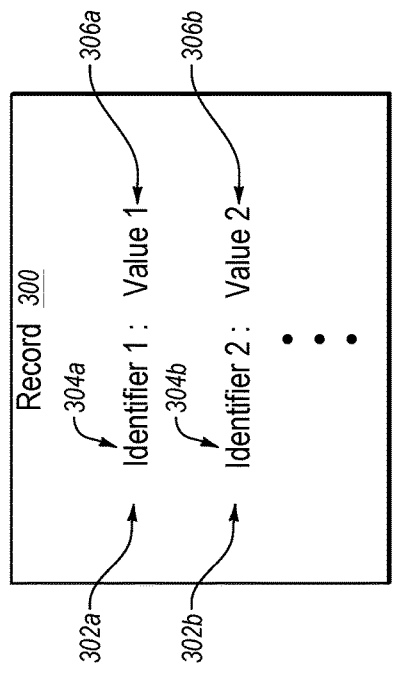
FIG. 3 illustrates an example electronic record.

FIG. 3 illustrates an example electronic record 300. The record 300 includes a first field 302*a* and a second field 302*b*, referred to as the fields 302. The first field 302*a* includes a first identifier 304*a* and a first value 306*a*. The second field 302*b* includes a second identifier 304*b* and a second value 306*b*. Although, the record 300 illustrates only the first and second fields 302, the record 300 may include any number of fields.

In the first field 302*a*, the first identifier 304*a* may identify or provide context for the first value 306*a*. In the second field 302*b*, the second identifier 304*b* may identify or provide context for the second value 306*b*. For example, the first identifier 304*a* may be "Name" and the first value 306*a* may be "Jane Doe." As another example, the second identifier 304*b* may be "Medication Currently Taking" and the second value 306*b* may be "Ibuprofen." As discussed in this disclosure, populating a field may include assigning data to the value of the field. For example, one or more words, numbers, phrases, characters, or other information may be assigned to a value of a field. Assigning data to the value of the field may include replacing previous data or assigning data for the first time when the value is a null. For example, the words "Jane Doe" may be assigned to the first value 306*a* to populate the first field 302*a*.

Returning to the discussion of FIG. 1, in some embodiments, the fields that may be populated may be identified. In some embodiments, all possible fields of the records in the records system 170 may be identified. Alternatively or additionally, a subset of fields of the records in the records system 170 may be identified. The subset of fields may be identified based on the subset of fields being associated with the first user. For example, in some embodiments, the profile data of the first user may be accessed and used to determine fields that may be associated with the first user. For example, medical information about the first user may be used to determine the subset of fields that may be populated. As an example, if the first user had a hip surgery, fields regarding unrelated topics, such as chemotherapy, organ transplants, and other medical conditions not associated with hip surgery may not be considered. In some embodiments, a particular record of the records system 170 with fields that are to be populated may be accessed using the profile data of the first user. In these and other embodiments, the fields of the particular record may be identified.

To populate the identified fields, data, such as one or more words, numbers, phrases, characters, or other information, may be identified in the first and second transcript data that corresponds to the identified fields. The data may be tagged based on its corresponding field. Tagging the data may include annotating or adding metadata to the first and second transcript data regarding the correlation between the data and the identified fields. Alternatively or additionally, tagging the data may include copying the data corresponding to the identified fields and storing the copied data at locations that are associated with the corresponding identified fields.

In some embodiments, identifying the data to populate the identified fields may be based on whether the data is from the first transcript data or the second transcript data. As described previously, the first transcript data is a transcript of first audio data from the first device and the second transcript data is a transcript of second audio data from the second device. Thus, the first transcript data is a transcript of words spoken by the first user during the communication session and the second transcript data is a transcript of words spoken by the second user during the communication session. Thus, there is no or little uncertainty regarding what is said by the first user and what is said by the second user. An increased certainty regarding what is said by each user may increase the probability of populating fields with the correct data from the first and second transcripts. In contrast, in other systems, a conversation between two people may be recorded in one audio stream such that a transcript includes words spoken by each person and it may be unclear which person spoke which word.

For example, a first identified field may be of a type such that the first identified field will be or is more likely to be populated with data from one of the first and second transcript data but not the other of the first and second transcript data. In these and other embodiments, the data from the one of the first and second transcript data may be tagged for the first identified field.

As an example, for a field with an identifier of "Patient Current Pain," the value for the identified field would most likely be provided by a transcript of words spoken by the patient. When the first user is the patient, the data for the identified field may be identified in the first transcript data because the first transcript data is from the first audio data generated from words spoken by the first user patient. For example, in a discussion between a health professional and a patient, the health professional may state "You may experience different types of pain, like a burning sensation or a throbbing pain." The patient may respond, "Mine is a sharp pain." If the words from the health professional and the patient are not distinguished there between, an error in tagging the patient current pain may occur. By contrast, knowing that the words "sharp pain" were spoken by the patient may increase the likelihood that the words are tagged for the correct field.

In some embodiments, a field of a record may be the entirety of the first transcript data and the second transcript data. In these and other embodiments, the transcription system 160 may combine the first transcript data and the second transcript data to generate third transcript data. The third transcript data may include a transcription of the entire communication session. In contrast, the first transcript data may include a transcription of the audio generated by the first device 110 and the second transcript data may include a transcription of the audio generated by one of the second devices 120.

Figure 5:
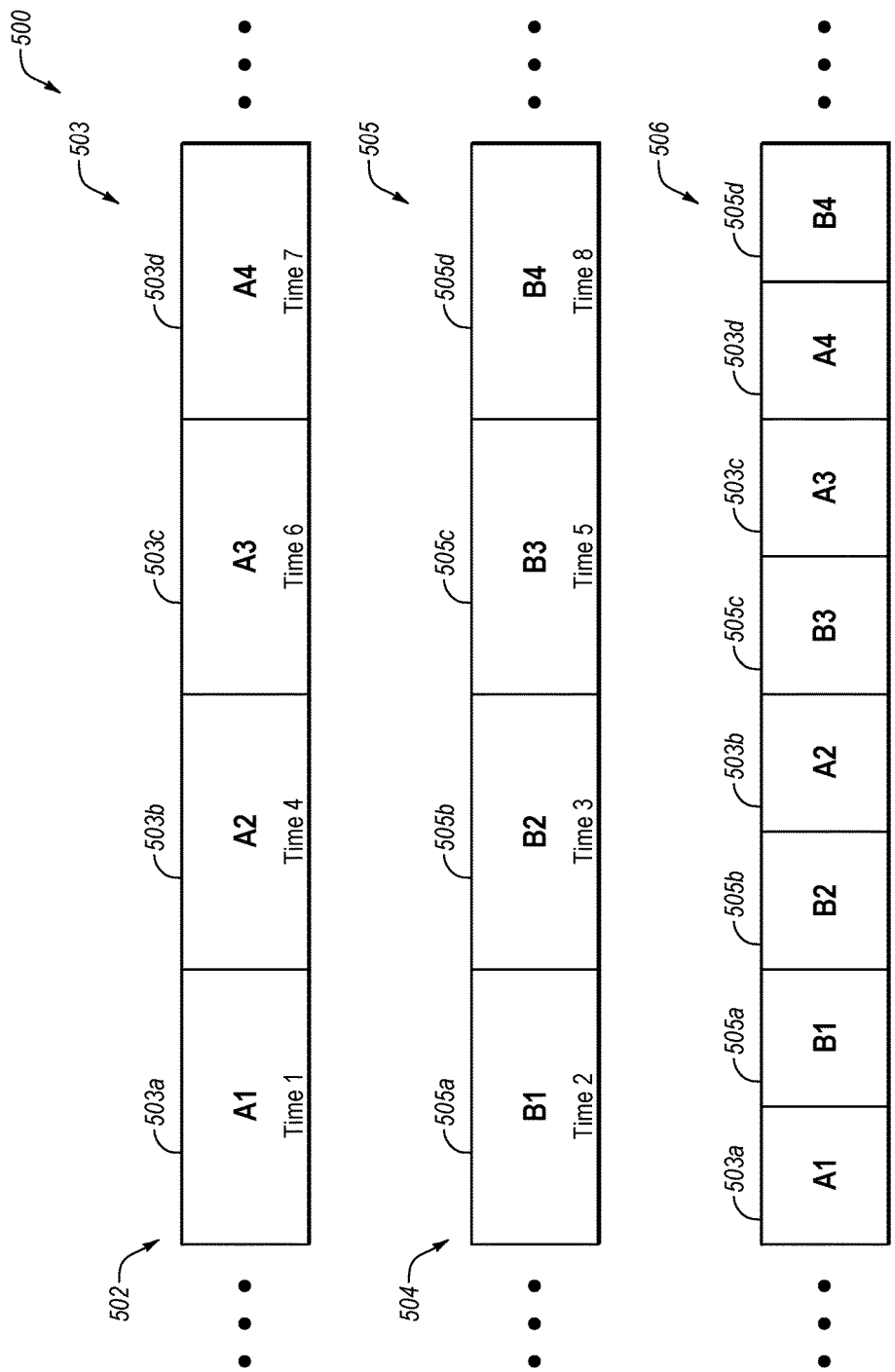
FIG. 5 illustrates an example diagram of combining transcript data.

In some embodiments, the first transcript data and the second transcript data may be combined by interweaving the data segments of the first transcript data and the second transcript data. In these and other embodiments, the data segments of the first transcript data and the second transcript data may be interweaved such that the data segments of the first transcript data and the second transcript data are combined in substantially chronological order. FIG. 5 illustrates an example regarding combining transcript data in a chronological order.

After the data is tagged, the transcription system 160 may be configured to provide the tagged data to the records system 170. In these and other embodiments, the transcription system 160 may provide the tagged data in a manner, for example with other data, such that the records system 170 may readily identify the record and the field associated with each instance of tagged data. For example, in some embodiments, the transcription system 160 may use an application programming interface (API) or other data structuring to provide the tagged data and other data to the records system 170.

After the records system 170 receives the tagged data and the other data, the records system 170 may identify a record to be populated. In these and other embodiments, the records system 170 may identify the record based on the other data. The other data may include data from the profile data of the first user, such as a user identifier, that may allow the records system 170 to identify a record that corresponds to the first user. After identifying the record to be populated, the records system 170 may populate the fields corresponding to the tagged data with the tagged data.

In some embodiments, the transcription system 160 may be configured to communicate with multiple different types of record systems. In these and other embodiments, the transcription system 160 may be configured to communicate with each of the records systems and to provide the tagged data with sufficient data to allow each of the records systems to populate their records.

For example, the transcription system 160 may be operated by a company that does not operate the record systems but that provides services to people that have records stored in various different record systems. The transcription system 160 may be configured to communicate with each of the record systems such that records in each system are populated correctly.

A brief example of the interaction of the components in the environment 100 is now provided. A video call between a patient using the first device 110 and a nurse using the first second-device 120a may be occurring through the communication routing system 140. The nurse may ask the patient questions regarding the patient's current health. The audio from the first device 110 and the first second-device 120a, e.g., the conversation between the nurse and the patient, may be transcribed by the transcription system 160. The transcription system 160 may tag portions of the transcription of the conversation and provide the tagged portions to the records system 170. The records system 170 may access an electronic health record of the patient and update the record to reflect current information about the condition of the patient.

The environment 100 thus illustrates an example where populating electronic records with data, in particular data resulting from a conversation between two people, may be automated by computing systems without human assistance or with reduced human assistance.

Modifications, additions, or omissions may be made to the environment 100 without departing from the scope of the present disclosure. For example, in some embodiments, the transcription system 160 may be part of the communication routing system 140. Alternatively or additionally, the transcription system 160, the communication routing system 140, and the records system 170 may all be part of one system.

As another example, in some embodiments, the transcription system 160 may receive the first audio data from the first device 110 and the second audio data from the second device 120 or the first audio data from the second device 120 and the second audio data from the first device 110.

Figure 2:
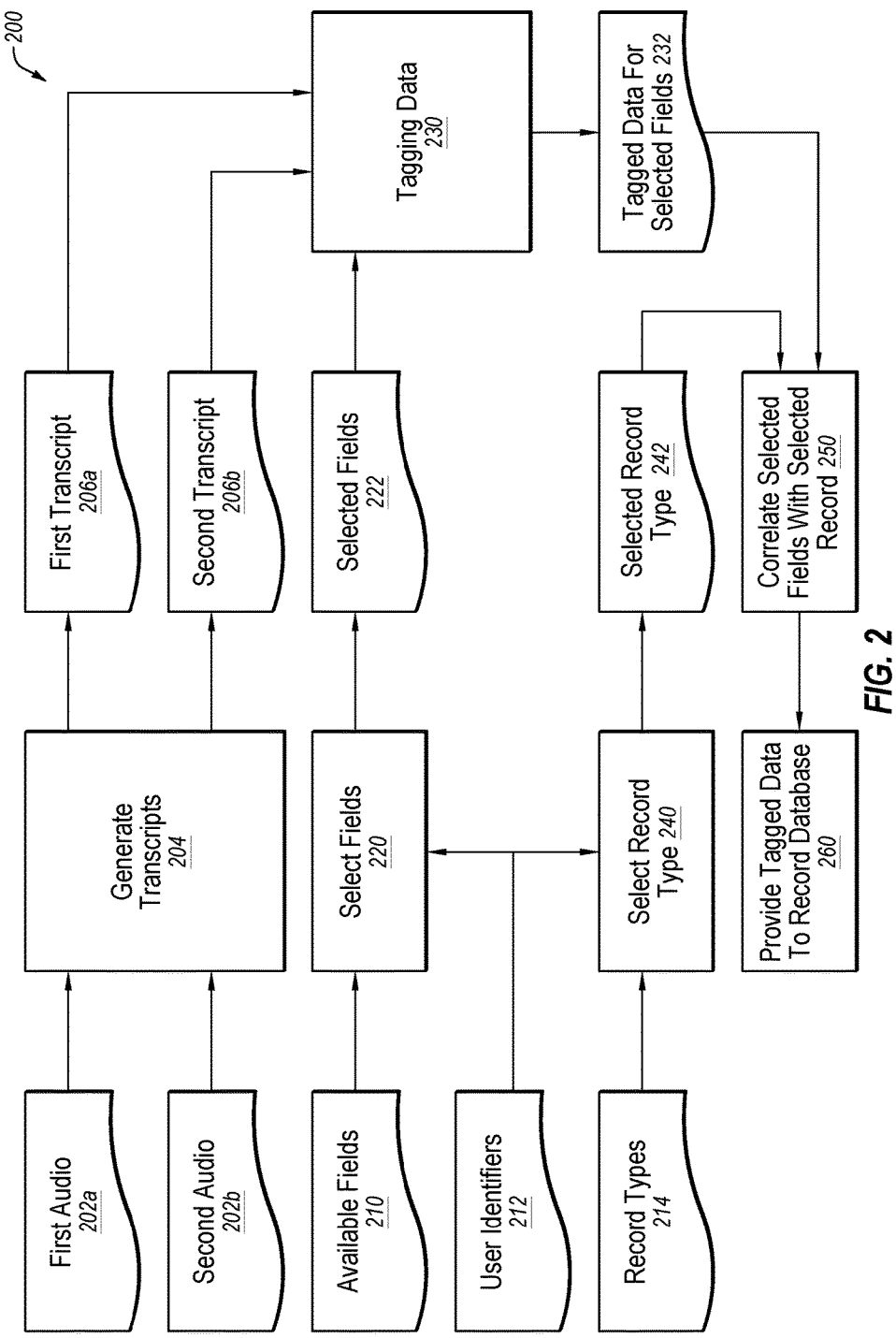
FIG. 2 is a diagram of an example flow that may be used with respect to transcription and population of electronic records.

FIG. 2 a diagram of an example flow 200 that may be used with respect to transcription and population of electronic records. The flow 200 may be arranged in accordance with at least one embodiment described in the present disclosure. In some embodiments, the flow 200 may be configured to illustrate one embodiment to identify words to populate fields of an electronic record. In these and other embodiments, a portion of the flow 200 may be an example of the operation of the transcription system 160 in the environment 100 of FIG. 1.

The flow 200 may begin at block 204, where a first transcript 206a may be generated and a second transcript 206b may be generated. The first transcript 206a may be generated based on first audio 202a. The second transcript 206b may be generated based on second audio 202b. The first transcript 206a and the second transcript 206b may be referred to jointly in this disclosure as the transcripts 206.

In some embodiments, the first transcript 206a and the second transcript 206b may be generated using a machine transcription of the first audio 202a and the second audio 202b, respectively. In some embodiments, before a machine transcription is made, the first audio 202a and the second audio 202b may be listened to and re-voiced by another person. In these and other embodiments, the other person may make corrections to the machine transcription by correcting words and adding punctuation, among other corrections.

In some embodiments, the transcripts 206 may include multiple data segments. Each of the data segments may include a transcription of a portion of the corresponding audio. As a result, each of the data segments may include one or more characters, such as one or more words, phrases, numbers, etc.

In some embodiments, the transcripts 206 may be separated into data segments based on a passage of time when a voice signal is detected in the audio being transcribed. For example, when a voice signal is detected in the audio being transcribed, a data segment may begin and continue until a particular period of time elapses or until no voice signal is detected in the audio for a particular time. After the particular period of time elapses or after a voice signal is again detected, another data segment may begin.

In these and other embodiments, a voice signal may be detected as present in audio based on an envelope of a magnitude of the audio. When the envelope is substantially flat over a particular period, there may be no voice signal. When the envelope varies over the particular period, there may be a voice signal. The particular period may be selected based on average talking speeds and voice inflections for an adult in the language being transcribed.

In some embodiments, the transcripts 206 may be separated into data segments based on a particular number of words that each data segment may include. For example, each data segment may include 1, 3, 5, 10, 15, 20, or more words in a data segment.

In some embodiments, the data segments may further include additional information. For example, the data segments may include information about the source device and/or the destination device, e.g., the first device 110, the second device 120, etc., for the audio that resulted in the data segments. Alternatively or additionally, the data segments may include a time stamp associated with when the audio was captured that resulted in the data segments.

In block 220, fields that may be populated by the first transcript 206a and the second transcript 206b may be selected. In these and other embodiments, various fields from among available fields 210 may be selected to be populated. In some embodiments, the available fields 210 may be all or mostly all of the fields of the record types that may be populated.

The fields that are selected, i.e., the selected fields 222, may be selected using information about the person from which the first audio 202a originates that may be accessed using a user identifier 212. The information about the person may be associated with the identifiers and/or values of fields. For example, if the fields relate to health care, the information about the person may include health care information. In these and other embodiments, the selected fields 222 may be selected based on a table that associates different types of fields with different data that may be included in the information about the person. For example, if the information about the person indicates that the person has cancer, the selected fields 222 may relate to cancer rather than to another medical condition. In some embodiments, all of the available fields 210 may be selected such that the selected fields 222 are the available fields 210.

In block 230, data from the transcripts 206 may be tagged as values for one or more of the selected fields 222. To tag data from the transcripts 206, the transcripts 206 may be analyzed to determine data, such as one or more words, numbers, phrases, characters, or other information, that may be a value for one or more of the selected fields 222. The data that may be a value for one or more of the selected fields 222 may be tagged for the one or more of the selected fields 222 to become tagged data 232. Tagging the data may associate the data with the one or more of the selected fields 222.

The analysis of the data to determine what data to tag may be performed using various methods. Various concepts are discussed in this disclosure that may be used separately or together. However, any number of other analysis techniques may be used.

In some embodiments, the transcripts 206 may be parsed to determine the individual words and sentence structure. After the transcripts 206 are parsed, the transcripts 206 may be analyzed using a natural language processing function that is developed using machine learning. The natural language processing function may be developed by training the natural language processing function over time.

To train the natural language processing function, various transcripts may be provided to the natural language processing function, various fields may be selected, and the data from the transcripts that are to be tagged for each of the selected various fields is identified for the natural language processing function. The natural language processing function may determine, e.g., learn, the trends or concepts in the transcripts that resulted in the tagging of the data being supplied using various techniques for classification, such as support vector machines, Bayesian networks, and learning classifier systems, among other techniques. After being trained, the natural language processing function may then analyze the transcripts 206 using the trends and concepts to tag the data from the transcripts 206 for the fields upon which the natural language processing function was trained.

In some embodiments, multiple natural language processing functions may be developed for different combinations of fields. In these and other embodiments, based on the selected fields 222, a natural language processing function that is trained for the selected fields 222 may be selected to analyze the transcripts 206.

In some embodiments, the natural language processing function may be trained using transcripts 206 that are grouped as forming a conversation but that each include only the words spoken by individuals in the conversation, such as the first transcript 206a and the second transcript 206b. In these and other embodiments, the natural language processing function may learn that data for particular fields may come more readily from one of the types of speakers in the conversation, e.g., a health care professional or a patient, than other speakers. When the natural language processing function is provided with the information regarding which transcript is associated with which speaker in the conversation, the natural language processing function may more accurately tag the data from the transcripts 206 for the selected fields 222. As a result, the data may be tagged based on the data corresponding to the record field and the data being from one of the transcripts 206 and not being from another of the transcripts 206.

In some embodiments, additional information about the selected fields 222 and the known sources of the first transcript 206a and the second transcript 206b may be used to tag data from the transcripts 206. For example, in some embodiments, data that corresponds to identifiers of the selected fields 222 may be located in one of the transcripts 206 and values for the selected fields 222 may be identified in the other of the transcripts 206 in a portion of the other transcript that follows in time the data that corresponds to the identifiers of the selected fields 222.

For example, a natural language processing function or some other analytic function, such as a word matching function, may be used to identify when a data segment in the second transcript 206b includes data that corresponds to an identifier from one of the selected fields 222. One or more data segments from the first transcript 206a that occurs after, based on a chronological order, the identified data segment from the second transcript 206b may be analyzed to tag data that may be used for the value of the one of the selected fields 222. The one or more data segments from the first transcript 206a may be analyzed using a natural language processing function trained for this analysis or using some other analytic function. Based on the analysis, data from the one or more data segments from the first transcript 206a may be tagged for the one of the selected fields 222.

Figure 4:
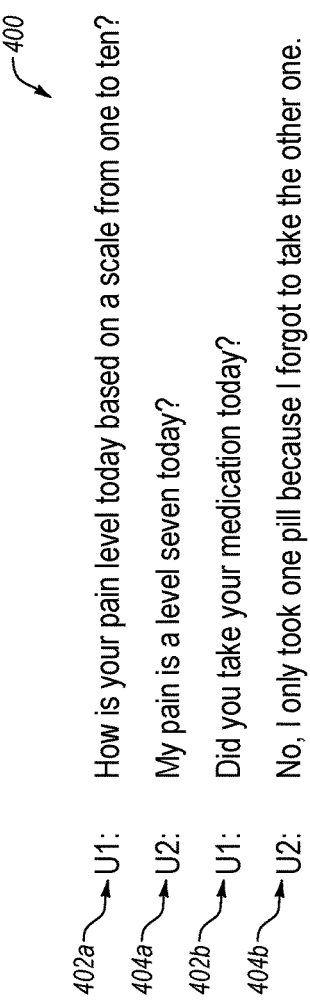
FIG. 4 illustrates example transcriptions.

An example is now provided with respect to FIGS. 2 and 4. FIG. 4 illustrates an example transcription dialogue 400. The example transcription dialogue 400 includes a chronological combination of two transcriptions from different audio sources. The first transcription includes first portion 402a and second portion 402b. The first transcription may be an example of the second transcript 206b of FIG. 2 and may be a transcript of audio from a health care professional. In this example, the first portion 402a and the second portion 402b may be first and second data segments, respectively, of the first transcription. The second transcription includes third portion 404a and fourth portion 404b. The second transcription may be an example of the first transcript 206a of FIG. 2 and may be a transcript of audio from a patient. In this example, the third portion 404a and the fourth portion 404b may be first and second data segments, respectively, of the second transcription.

In this example, an identifier of a selected field may be a current pain level of the patient. As a result, the first portion 402a of the first transcription may be identified as the data segment of the first transcription that includes the identifier of the selected field. The third portion 404a of the second transcription may be the data segment of the second transcription that occurs after, in a chronological order, the identified data segment of the first transcription. Thus, the third portion 404a may be analyzed to determine the value of the selected field, which in this example, may be "pain is a level seven."

In this example, there were no additional data segments of the first transcription between the identified data segment of the first transcription and the next data segment of the second transcription. However, the disclosure is not limited to this embodiment, as there may be other data segments of the first transcription that may occur before the next data segment of the second transcription.

Referring again to FIG. 4, in some embodiments, data that corresponds to identifiers of the selected fields 222 may be located in one of the transcripts 206 based on a correlation with data presented to a user that generates the audio that results in the one of the transcripts 206.

For example, the second audio 202b may be based on words spoken by a user. The user may be prompted to speak a particular phrase by an electronic device that generates the second audio 202b. For example, the electronic device may display the phrase to the user. The phrase may be determined based on the identifier of a selected field and be configured to solicit a response that would include a value of the selected field. In these and other embodiments, the phrase may be provided to the electronic device by a system that is performing the flow 200.

The electronic device or the system that provides the phrase to the electronic device may note the time that the phrase is displayed or delivered to the electronic device for display in real-time to allow the time of display of the phrase to be correlated with time stamps of data segments of the second transcript 206b. Additionally, the phrase may be identified in the second transcript 206b through a simple matching algorithm because the phrase is known by the system performing the flow 200. Based on the time correlation and the known phrase, in some embodiments, the data segment of the second transcript 206b that corresponds to the identifier of the selected field may be identified without the use of a natural language processing function or other similar analysis.

After identifying the data segment of the second transcript 206b that corresponds to the identifier of the selected field, one or more subsequent data segments from the first transcript 206a that occur after the identified data segment from the second transcript 206b may be analyzed for the value of the selected field.

For example, with respect to FIG. 4 and following from the previous example provided with respect to FIG. 4, an electronic device that may be capturing the speech of the health care professional at a particular time may display the question "How is your pain level today based on a scale from one to ten?" The phrase may be known as being an identifier for a first field. Thus, the first portion 402a may be identified as including the identifier of the first field based on the matching language between the phrase displayed and the transcript and a correlation between the particular time that the phrase is displayed and timing of the phrase in the second transcript 206b. In this example, the third portion 404a, which is the data segment of the first transcript 206a that occurs after the first portion 402a, may be analyzed to determine the value of the first field. Which in this example, may be "pain is a level seven."

Referring again to FIG. 2, in some embodiments, additional verification may be done after tagging by the natural language processing function. For example, the natural language processing function may suggest a tag for data from the transcripts 206. In these and other embodiments, the suggested tag may be verified by a human. In some embodiments, the human verifying the suggested tag may be a participant in the transcribed conversation, such as the health care professional. Alternatively or additionally, the suggested tag may be verified by a person that re-voiced the conversation for machine transcription as discussed previously. In these and other embodiments, the natural language processing function may provide one or more suggested tags for data from the transcripts 206. The human verifying the suggested tags may select the appropriate tag from the suggested tags for the data or may decline all of the suggested tags. In these and other embodiments, the human may be able to select a tag for the data from among tags that correspond to the selected fields 222.

In block 240, a record type may be selected from multiple record types 214 as a selected record type 242. In some embodiments, the record type may be selected using information about the person from which the first audio 202a originates that may be accessed using the user identifier 212. For example, the information may be a name of a record system that stores records for the person. Alternatively or additionally, the information may allow the name of the record system that stores records for the person to be identified. In these and other embodiments, the record type may be the type of record used by the records system that includes the record of the person from which the first audio 202a originates.

In block 250, the selected fields 222 may be correlated with the selected record type 242. In these and other embodiments, the selected fields 222 may be general fields that may correspond to multiple different types of records. Multiple different types of records may exist because different entities may manage different records. Fields with the same or similar values in these different record types may be located in different locations and/or include slightly different descriptions, e.g., identifiers. The selected fields 222 may be general fields that may correspond to different fields across different record types with the same or similar values.

The selected fields 222 may be correlated with the specific fields of the different record types based on a look-up table or some other algorithm. By correlating the selected fields 222 with the fields of the selected record type 242, the tagged data may be populated in the correct field in the selected record type 242. Furthermore, by correlating the selected fields 222 with fields of different types of records, the tagged data may be populated in the correct field in any number of different types of records.

In block 260, the tagged data may be provided to a record database to update a record of the person from which the first audio 202a originates.

Modifications, additions, or omissions may be made to the flow 200 without departing from the scope of the present disclosure. For example, in some embodiments, the flow may not include the block 220. In these and other embodiments, the available fields 210 may be used for tagging the data. As another example, the flow 200 may not include the blocks 240 and 250. In these and other embodiments, the tagged data 232 may be provided directly to the record database.

FIG. 5 illustrates an example diagram 500 of combining transcript data. The diagram 500 may be arranged in accordance with at least one embodiment described in the present disclosure. The diagram 500 illustrates first transcript data 502, second transcript data 504, and third transcript data 506. In particular, the diagram 500 illustrates an example combination of the first transcript data 502 with the second transcript data 504 to generate the third transcript data 506.

The first transcript data 502 includes first data segments 503, including first first-data segment 503a, second first-data segment 503b, third first-data segment 503c, and fourth first-data segment 503d. Each of the first data segments 503 includes one or more words, represented by A1, A2, A3, and A4. The second transcript data 504 includes second data segments 505, including first second-data segment 505a, second second-data segment 505b, third second-data segment 505c, and fourth second-data segment 505d. Each of the second data segments 505 includes one or more words, represented by B1, B2, B3, and B4.

Each of the first data segments 503 and the second data segments 505 further include a time. The times are represented as Time 1 through Time 8. The numbering of the times as Time 1 through Time 8 represent arbitrary times, but the numbering of 1-8 illustrates a chronological order from Time 1 to Time 8.

As illustrated in diagram 500, the first transcript data 502 and the second transcript data 504 are combined by determining a data segment of the first data segments 503 and the second data segments 505 that has the earliest time. The data segment with the earliest time is used to start the third transcript data 506. The data segment of the first data segments 503 and the second data segments 505 with the next time is then added to the third transcript data 506. Remaining data segments are added in chronological order as illustrated.

In some embodiments, one or more of the data segments from the first data segments 503 and the second data segments 505 may have a substantially similar or similar time. In these and other embodiments, an ordering of the data segments may be selected based on the words and/or punctuation in the data segments and adjacent data segments of the data segments in question. For example, if the second first-data segment 503b and the second second-data segment 505b have substantially similar or similar times, the wording and or punctuation of the second first-data segment 503b and/or the second second-data segment 505b and their adjacent data segments may be reviewed. If either of the second first-data segment 503b or the second second-data segment 505b included punctuation, then the data segment with the punctuation may be placed ahead of the other data segment in the third transcript data 506. As another example, punctuation of the data segments surrounding the data segments in question may be analyzed to determine an ordering of the data segments.

Modifications, additions, or omissions may be made to the diagram 500 and/or the described method of combining transcript data without departing from the scope of the present disclosure.

Figure 6:
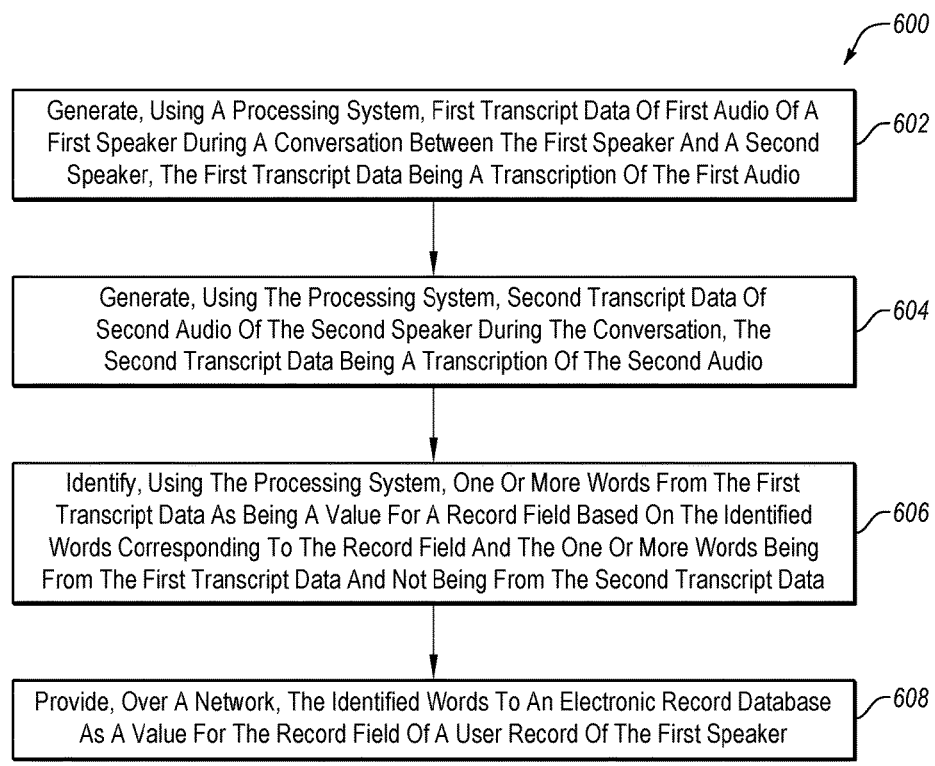
FIG. 6 is a flowchart of an example method of transcription and population of electronic records.

FIG. 6 is a flowchart of another example method 600 of transcription and population of electronic records. The method 600 may be arranged in accordance with at least one embodiment described in the present disclosure. The method 600 may be performed, in whole or in part, in some embodiments by a system or combinations of components in a system or environment as described in the present disclosure. For example, the method 600 may be performed, in whole or in part, by environment 100 and/or the system 800 of FIGS. 1 and 8, respectively. In these and other embodiments, some or all of the operations of the method 600 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 600 may begin at block 602, where first transcript data of first audio of a first speaker during a conversation between a first speaker and a second speaker may be generated using a processing system. The first transcript data may be a transcription of the first audio.

In block 604, second transcript data of second audio of the second speaker during the conversation may be generated using the processing system. The second transcript data may be a transcription of the second audio. In some embodiments, the second speaker may be a health care professional and the first speaker may be a patient of the health care professional.

In block 606, one or more words from the first transcript data may be identified, using the processing system, as being a value for a record field based on the identified words corresponding to the record field and the one or more words being from the first transcript data and not being from the second transcript data.

In block 608, the identified words may be provided over a network to an electronic record database as a value for the record field of a user record of the first speaker.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, before identifying the one or more words, the method 600 may further include obtaining a first user identifier associated with the first speaker and identifying multiple general record fields that are to be populated using information from the first audio and the second audio during the conversation. In these and other embodiments, the multiple general record fields may be identified based on the first user identifier. In these and other embodiments, the record field may be one of the identified multiple general record fields.

As another example, the method 600 may further include identifying one or more second words from the second transcript data as being a value for a second record field based on the identified second words corresponding to the second record field and the one or more words being from the second transcript data and not the first transcript data. In these and other embodiments, the method 600 may additionally include providing the identified second words to the electronic record database as a value for the second record field of a user record.

As another example, the method 600 may further include establishing a communication session between a first device and a second device such that first device audio is sent from the first device to the second device and second device audio is sent from the second device to the first device during the communication session. In these and other embodiments, the first audio may be the first device audio and the second audio may be the second device audio.

As another example, in some embodiments, before identifying the one or more words, the method 600 may further include obtaining a first user identifier associated with the first device based on data from the first device that is used to establish the communication session and selecting a first electronic record type from multiple electronic record types based on the first user identifier. In these and other embodiments, the user record may be of the first electronic record type. The method 600 may further include determining the record field in the first electronic record type that corresponds to the identified words.

Figure 7:
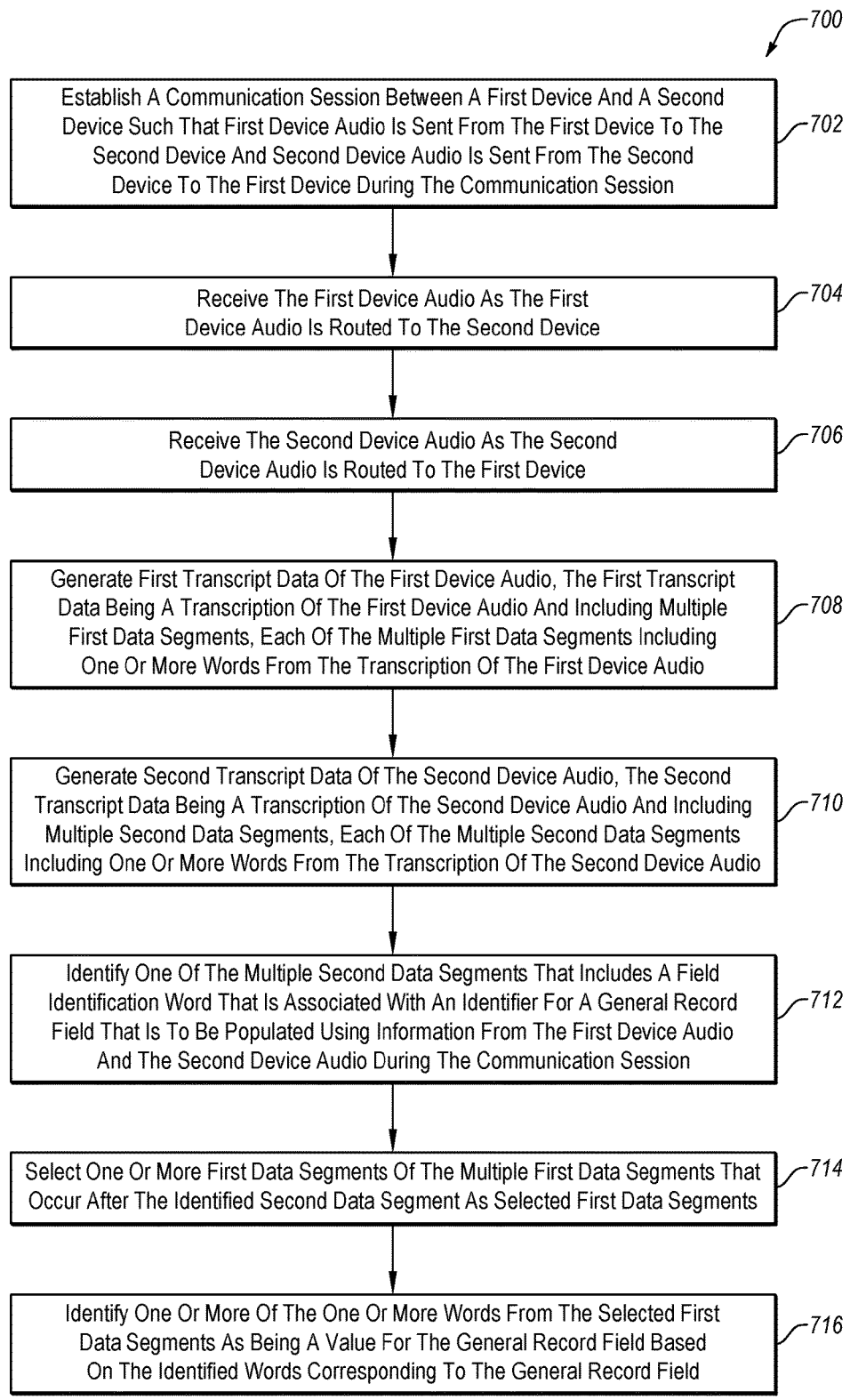
FIG. 7 is a flowchart of another example method of transcription and population of electronic records.

FIG. 7 is a flowchart of an example method 700 of transcription and population of electronic records. The method 700 may be arranged in accordance with at least one embodiment described in the present disclosure. The method 700 may be performed, in whole or in part, in some embodiments by a system or combinations of components in a system or environment as described in the present disclosure. For example, the method 700 may be performed, in whole or in part, by environment 100 and/or the system 800 of FIGS. 1 and 8, respectively. In these and other embodiments, some or all of the operations of the method 700 may be performed based on the execution of instructions stored on one or more non-transitory computer-readable media. Although illustrated as discrete blocks, various blocks may be divided into additional blocks, combined into fewer blocks, or eliminated, depending on the particular implementation.

The method 700 may begin at block 702, where a communication session may be established between a first device and a second device such that first device audio is sent from the first device to the second device and second device audio is sent from the second device to the first device during the communication session.

In block 704, the first device audio may be received as the first device audio is routed to the second device. In block 706, the second device audio may be received as the second device audio is routed to the first device.

In block 708, first transcript data of the first device audio may be generated. The first transcript data may be a transcription of the first device audio and may include multiple first data segments. Each of the multiple first data segments may include one or more words from the transcription of the first device audio.

In block 710, second transcript data of the second device audio may be generated. The second transcript data may be a transcription of the second device audio and may include multiple second data segments. Each of the multiple second data segments may include one or more words from the transcription of the second device audio.

In block 712, one of the multiple second data segments may be identified that includes a field identification word that is associated with an identifier for a general record field that is to be populated using information from the first device audio and the second device audio during the communication session.

In block 714, one or more first data segments of the multiple first data segments that occur after the identified second data segment may be selected and thus be selected first data segments.

In block 716, one or more of the one or more words from the selected first data segments may be identified as being a value for the general record field based on the identified words corresponding to the general record field.

One skilled in the art will appreciate that, for these processes, operations, and methods, the functions and/or operations performed may be implemented in differing order. Furthermore, the outlined functions and operations are only provided as examples, and some of the functions and operations may be optional, combined into fewer functions and operations, or expanded into additional functions and operations without detracting from the essence of the disclosed embodiments.

For example, in some embodiments, the method 700 may further include obtaining a first user identifier associated with the first device based on data from the first device that is used to establish the communication session and selecting a first electronic record type from multiple electronic record types based on the first user identifier. The method 700 may further include matching the general record field with a first record field of the first electronic record type based on the general record field and the first record field being configured for analogous values and providing the first user identifier to an electronic health record database that stores the first electronic record type. The method 700 may further include providing to the electronic health record database the identified words as a value for the first record field of a user record of the first electronic record type. In these and other embodiments, the user record may be associated with the first user identifier in the electronic health record database.

As another example, in some embodiments, the method 700 may further include interweaving the first transcript data and the second transcript data to generate third transcript data such that a combined transcription included in the third transcript data is substantially in chronological order and providing to the electronic health record database the third transcript data as a value of a second record field of the user record.

As another example, in some embodiments, the method 700 may further include providing to the second device the field identification word for presentation of the field identification word by the second device. In these and other embodiments, the identified second data segment is identified based on the identified second data segment including the field identification word and the identified second data segment occurring, in time, after the presentation of the field identification word by the second device.

Figure 8:
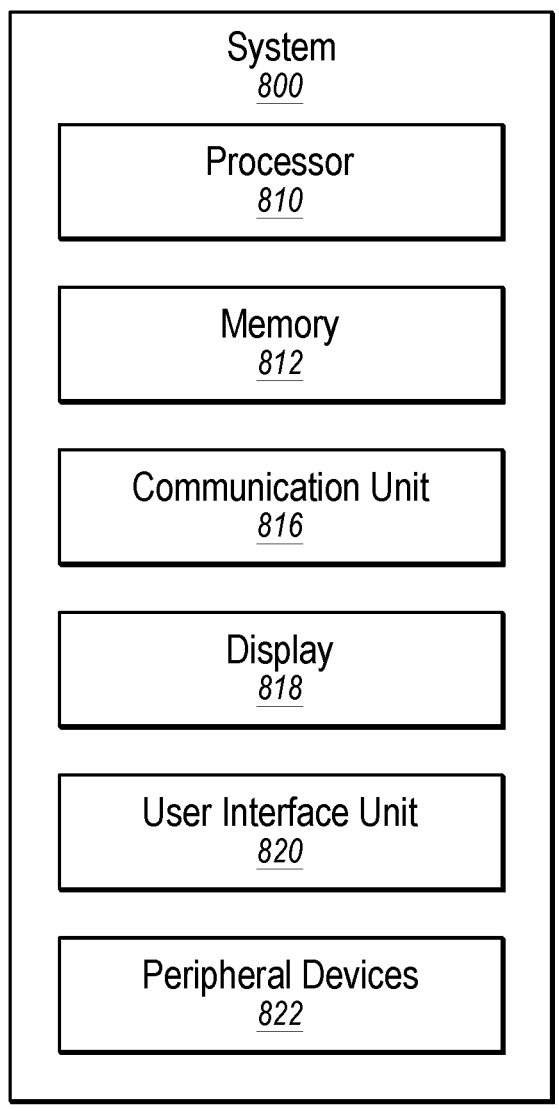
FIG. 8 illustrates an example computing system that may be used to transcribe or identify data for population of electronic records, all arranged according to one or more embodiments described in the present disclosure.

FIG. 8 illustrates an example computing system 800 that may be used to transcribe or identify data for population of electronic records. The system 800 may be arranged in accordance with at least one embodiment described in the present disclosure. The system 800 may include a processor 810, memory 812, a communication unit 816, a display 818, a user interface unit 820, and a peripheral device 822, which all may be communicatively coupled. In some embodiments, the system 800 may be part of any of the systems or devices described in this disclosure.

For example, the system 800 may be part of the first device 110 of FIG. 1. In these and other embodiments, the system 800 may be configured to perform one or more of the following tasks: participate in a communication session by: capturing audio and video of a first user, sending the captured audio and video, receiving audio and video of a second user, and presenting the received audio and video, among other tasks described in the present disclosure.

As another example, the system 800 may be part of the second devices 120 of FIG. 1. In these and other embodiments, the system 800 may be configured to perform one or more of the following tasks: participate in a communication session by: capturing audio and video of a second user, sending the captured audio and video, receiving audio and video of a first user, and presenting the received audio and video, among other tasks described in the present disclosure.

As another example, the system 800 may be part of the transcription system 160 of FIG. 1. In these and other embodiments, the system 800 may be configured to perform one or more of the following tasks: generate transcript data of audio from the first device and the second device, identify data from the transcript data for populating record fields, and combine the first and second transcript data, among other tasks described in the present disclosure.

Generally, the processor 810 may include any suitable special-purpose or general-purpose computer, computing entity, or processing device including various computer hardware or software modules and may be configured to execute instructions stored on any applicable computer-readable storage media. For example, the processor 810 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

Although illustrated as a single processor in FIG. 8, it is understood that the processor 810 may include any number of processors distributed across any number of networks or physical locations that are configured to perform individually or collectively any number of operations described herein. In some embodiments, the processor 810 may interpret and/or execute program instructions and/or process data stored in the memory 812. In some embodiments, the processor 810 may execute the program instructions stored in the memory 812.

For example, the system 800 may be part of the systems described in FIG. 1. In these and other embodiments, instructions may be used to perform one or more of the methods 600 and 700 of FIGS. 6 and 7, respectively and/or the flow 200 of FIG. 2.

The memory 812 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 810. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 810 to perform a certain operation or group of operations as described in this disclosure.

The communication unit 816 may include any component, device, system, or combination thereof that is configured to transmit or receive information over a network. In some embodiments, the communication unit 816 may communicate with other devices at other locations, the same location, or even other components within the same system. For example, the communication unit 816 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, cellular communication facilities, etc.), and/or the like. The communication unit 816 may permit data to be exchanged with a network and/or any other devices or systems described in the present disclosure. For example, if the system 800 is included in the first device 110 of FIG. 1, the communication unit 816 may allow the first device 110 to communicate with the communication routing system 140.

The display 818 may be configured as one or more displays, like an LCD, LED, or other type of display. The display 818 may be configured to present video, text captions, user interfaces, and other data as directed by the processor 810. For example, when the system 800 is included in the first device 110 of FIG. 1, the display 818 may be configured to present second video from a second device and a transcript of second audio from the second device.

The user interface unit 820 may include any device to allow a user to interface with the system 800. For example, the user interface unit 820 may include a mouse, a track pad, a keyboard, buttons, and/or a touchscreen, among other devices. The user interface unit 820 may receive input from a user and provide the input to the processor 810.

The peripheral devices 822 may include one or more devices. For example, the peripheral devices may include a microphone, an imager, and/or a speaker, among other peripheral devices. In these and other embodiments, the microphone may be configured to capture audio. The imager may be configured to capture digital images. The digital images may be captured in a manner to produce video or image data. In some embodiments, the speaker may broadcast audio received by the system 800 or otherwise generated by the system 800. Modifications, additions, or omissions may be made to the system 800 without departing from the scope of the present disclosure. For example, the system 800 may not include one or more of: the display 818, the user interface unit 820, and peripheral device 822.

In some embodiments, the different components, modules, engines, and services described herein may be implemented as objects or processes that execute on a computing system (e.g., as separate threads). While some of the systems and methods described herein are generally described as being implemented in software (stored on and/or executed by general purpose hardware), specific hardware implementations or a combination of software and specific hardware implementations are also possible and contemplated.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. A computer-implemented method to populate an electronic record based on communications between two people, the method comprising:
    establishing a communication session between a first device and a second device such that first device audio is sent from the first device to the second device and second device audio is sent from the second device to the first device during the communication session;
    receiving the first device audio as the first device audio is routed to the second device;
    receiving the second device audio as the second device audio is routed to the first device;
    generating first transcript data of the first device audio, the first transcript data being a transcription of the first device audio and including a plurality of first data segments, each of the plurality of first data segments including one or more words from the transcription of the first device audio;
    generating second transcript data of the second device audio, the second transcript data being a transcription of the second device audio and including a plurality of second data segments, each of the plurality of second data segments including one or more words from the transcription of the second device audio;
    identifying one of the plurality of second data segments that includes a field identification word that is associated with an identifier for a general record field that is to be populated using information from the first device audio and the second device audio during the communication session;
    selecting one or more first data segments of the plurality of first data segments that occur after the identified second data segment as selected first data segments; and
    identifying one or more of the one or more words from the selected first data segments as being a value for the general record field based on the identified words corresponding to the general record field.

2. The method of claim 1, further comprising:
    obtaining a first user identifier associated with the first device based on data from the first device that is used to establish the communication session;
    selecting a first electronic record type from a plurality of electronic record types based on the first user identifier;
    matching the general record field with a first record field of the first electronic record type based on the general record field and the first record field being configured for analogous values;
    providing the first user identifier to an electronic health record database that stores the first electronic record type; and
    providing to the electronic health record database the identified words as a value for the first record field of a user record of the first electronic record type, the user record being associated with the first user identifier in the electronic health record database.

3. The method of claim 2, further comprising interweaving the first transcript data and the second transcript data to generate third transcript data such that a combined transcription included in the third transcript data is substantially in chronological order.

4. The method of claim 3, further comprising providing to the electronic health record database the third transcript data as a value of a second record field of the user record.

5. The method of claim 1, further comprising providing to the second device the field identification word for presentation of the field identification word by the second device.

6. The method of claim 5, wherein the identified second data segment is identified based on the identified second data segment including the field identification word and the identified second data segment occurring, in time, after the presentation of the field identification word by the second device.

7. One or more non-transitory media configured to store instructions that in response to being executed by one or more processors cause one or more systems to perform the method of claim 1.

8. A computer-implemented method to populate an electronic record based on communications between two people, the method comprising:
  generating, using a processing system, first transcript data of first audio of a first speaker during a conversation between the first speaker and a second speaker, the first transcript data being a transcription of the first audio;
  generating, using the processing system, second transcript data of second audio of the second speaker during the conversation, the second transcript data being a transcription of the second audio;
  obtaining a first user identifier associated with the first speaker;
  identifying a plurality of general record fields that are to be populated using information from the first audio and the second audio during the conversation, the plurality of general record fields being identified based on the first user identifier;
  after identifying the plurality of general record fields, identifying, using the processing system, one or more words from the first transcript data as being a value for a record field based on the identified words corresponding to the record field and the one or more words being from the first transcript data and not being from the second transcript data, wherein the record field is one of the identified plurality of general record fields; and
  providing, over a network, the identified words to an electronic record database as a value for the record field of a user record of the first speaker.

9. The method of claim 8, further comprising:
  identifying one or more second words from the second transcript data as being a value for a second record field based on the identified second words corresponding to the second record field and the one or more second words being from the second transcript data and not the first transcript data; and
  providing the identified second words to the electronic record database as a value for the second record field of a user record.

10. The method of claim 8, further comprising establishing a communication session between a first device and a second device such that first device audio is sent from the first device to the second device and second device audio is sent from the second device to the first device during the communication session, wherein the first audio is the first device audio and the second audio is the second device audio.

11. The method of claim 8, wherein the record field is a first record field and before providing the identified words the method further comprises:
  selecting a first electronic record type from a plurality of electronic record types based on the first user identifier, the user record being of the first electronic record type; and
  determining a second record field in the first electronic record type that corresponds to the first record field.

12. The method of claim 8, wherein the second speaker is a health care professional and the first speaker is a patient of the health care professional.

13. One or more non-transitory media configured to store instructions that in response to being executed by one or more processors cause one or more systems to perform the method of claim 8.

14. A computer-implemented method to populate an electronic record based on communications between two people, the method comprising:
  establishing a communication session between a first device and a second device such that first device audio is sent from the first device to the second device and second device audio is sent from the second device to the first device during the communication session;
  generating first transcript data of the first device audio, the first transcript data being a transcription of the first device audio;
  generating second transcript data of the second device audio, the second transcript data being a transcription of the second device audio;
  obtaining a first user identifier associated with the first device based on data from the first device that is used to establish the communication session;
  identifying a plurality of general record fields that are to be populated using information from the first device audio and the second device audio during the communication session, the plurality of general record fields are identified based on the first user identifier;
  after identifying the plurality of general record fields, identifying one or more words from the first transcript data as being a value for a record field based on the identified words corresponding to the record field and the one or more words being from the first transcript data and not being from the second transcript data, wherein the record field is one of the identified plurality of general record fields; and
  providing the identified words to an electronic record database as a value for the record field of a user record.

15. The method of claim 14, wherein the record field is a first record field and before providing the identified words the method further comprises:
  selecting a first electronic record type from a plurality of electronic record types based on the first user identifier, the user record being of the first electronic record type; and
  determining a second record field in the first electronic record type that corresponds to the first record field.

16. The method of claim 14, further comprising:
  identifying one or more second words from the second transcript data as being a value for a second record field based on the identified second words corresponding to the second record field and the one or more second words being from the second transcript data and not the first transcript data; and
  providing the identified second words to the electronic record database as a value for the second record field of a user record.

17. One or more non-transitory media configured to store instructions that in response to being executed by one or more processors cause one or more systems to perform the method of claim 14.

18. A computer-implemented method to populate an electronic record based on communications between two people, the method comprising:
- establishing a communication session between a first device and a second device such that first device audio is sent from the first device to the second device and second device audio is sent from the second device to the first device during the communication session;
- generating first transcript data of the first device audio, the first transcript data being a transcription of the first device audio and including a plurality of first data segments, each of the plurality of first data segments including one or more words from the transcription of the first device audio;
- generating second transcript data of the second device audio, the second transcript data being a transcription of the second device audio and including a plurality of second data segments, each of the plurality of second data segments including one or more words from the transcription of the second device audio;
- identifying one of the plurality of second data segments that includes a field identification word that is associated with an identifier for a record field;
- selecting an initial first data segment of the plurality of first data segments that occurs after the identified second data segment as a selected first data segment;
- identifying one or more words from the first transcript data as being a value for the record field based on the identified words corresponding to the record field, being from the selected first data segment, and being from the first transcript data and not being from the second transcript data; and
- providing the identified words to an electronic record database as a value for the record field of a user record.

19. The method of claim 18, further comprising:
- identifying one or more second words from the second transcript data as being a value for a second record field based on the identified second words corresponding to the second record field and the one or more second words being from the second transcript data and not the first transcript data; and
- providing the identified second words to the electronic record database as a value for the second record field of a user record.

20. One or more non-transitory media configured to store instructions that in response to being executed by one or more processors cause one or more systems to perform the method of claim 18.

* * * * *